United States Patent [19]
Schmerse, Jr.

[11] Patent Number: 5,127,899
[45] Date of Patent: Jul. 7, 1992

[54] SWAB

[76] Inventor: Roscoe E. Schmerse, Jr., 4487 Ridgegate Rd., Anaheim Hills, Calif. 92807

[21] Appl. No.: 653,657

[22] Filed: Feb. 8, 1991

Related U.S. Application Data

[63] Continuation of Ser. No. 339,816, Apr. 18, 1989, abandoned.

[51] Int. Cl.⁵ .................................... A61M 35/00
[52] U.S. Cl. ................................................ 604/1
[58] Field of Search .............. 19/145.3; 128/759; 604/1-3; 606/162

[56] References Cited

U.S. PATENT DOCUMENTS

| | | | |
|---|---|---|---|
| 1,962,875 | 6/1934 | Reber | 128/269 |
| 1,995,733 | 3/1935 | Brekke | 128/269 |
| 2,043,678 | 6/1936 | Schmalz | 128/269 |
| 2,362,704 | 11/1944 | McGivern | 128/260 |
| 2,842,790 | 7/1958 | Castelli | 15/143 |
| 2,876,501 | 3/1959 | Glickston | 19/149 |
| 3,368,549 | 2/1968 | Barr et al. | 128/2 |
| 4,718,889 | 1/1988 | Blasius, Jr. | 604/1 |

FOREIGN PATENT DOCUMENTS

| | | | |
|---|---|---|---|
| 237589 | 9/1987 | United Kingdom | 604/1 |
| 277009 | 8/1988 | United Kingdom | 604/1 |

Primary Examiner—Stephen C. Pellegrino
Assistant Examiner—Michael Rafa
Attorney, Agent, or Firm—Stetina and Brunda

[57] ABSTRACT

An improved swab having cotton covered enlarged distal ends and an elongate stem for use in cleaning the outer portion of the ear and/or in applying cosmetics and the like. Positioned at the distal end of the swab beneath the cotton coverings is a disc which is sized to prevent entry of the swab into the human ear canal. The disc also prevents the stem from protruding through the cotton covering and causing injury during use.

10 Claims, 1 Drawing Sheet

SWAB

This application is a continuation of application Ser. No. 07/339,816, filed Apr. 18, 1989, now abandoned.

FIELD OF THE INVENTION

The present invention relates generally to swabs used for cleaning the outer portion of the ear and for applying cosmetics and the like and more particularly to an improved swab having cotton covered enlarged distal ends and an elongate stem. Positioned at the distal ends of the swab beneath the cotton coverings are flat discs which are sized to prevent entry of the swab into the human ear canal. The flat discs also prevent the stem from protruding through the absorbent covering and causing injury during use.

BACKGROUND OF THE INVENTION

Swabs having an absorbent covering on the tip and an elongated stem are well known. Cotton is generally used as the absorbent cellulose tip material, although other fibrous absorbent cellulose materials such as rayon are known. Stem materials such as wood, rolled paper, and plastic are common. Conventional swabs are typically constructed by applying the absorbent covering directly to the distal ends of the stem. An adhesive may be used to more firmly hold the absorbent covering in place upon the swab.

The problems associated with prior art swabs are well known. Warnings on swab packages attest to the fact that serious damage can result from their misuse. Not only must adults be educated in the proper use of these swabs, but children typically should not be allowed to use them without proper supervision. A popular brand of cotton swab attest to the inherent safety deficiencies associated with prior art swabs by including the following package warning:

EAR CARE: CAUTION when using on ears. To help insure safe use hold the swab about ½" from the tip. Use gently to remove visible dirt and wax around the outer surface of the ear. Avoid probing deeply into the ear canal. Doing so may push wax/dirt deeper into the ear canal and obstruct hearing. Do not use inside the ear canal of children. Should problems occur, consult your physician. Use only as directed . . . improper use can cause injury. SAFETY TIP: Keep all baby care products out of the reach of children.

Another popular brand advises:

THE CAREFUL WAY TO CLEAN EARS: Hold swab firmly and use a soft touch. Stroke swab gently around the outer surfaces of the ear, without entering the ear canal.

Although these disclaimers have proven useful in alerting adult consumers to the hazards of the improper use of swabs and limiting the potential liability of swab manufacturers, potential damage to the eardrum remains inherent in the use of prior art swabs.

It is quite apparent that the entry of a swab into the human ear canal is very dangerous. The ear drum is extremely delicate. Injuries due to improper use of prior art swabs are common.

An additional problem commonly associated with prior art swabs is a tendency of the stem of the swab to protrude through the absorbent covering during use and thereby injure delicate body tissue.

Prior art patents have generally addressed the problem of adhering the absorbent covering to the stem and paid comparatively little attention to the problems of potential injury. Adhering the absorbent covering to the stem has been accomplished by a variety of methods. Typically such prior art methods developed to adhere the absorbent covering to the stem have generally exaggerated the potential of causing injury to the ear. For example, U.S. Pat. No. 2,842,790 issued to Castelli employs the use of barbs to better secure the absorbent covering to the stem and U.S. Pat. No. 2,362,704 issued to McGivern employs a projection on the end of a metal stem to secure the absorbent covering. Both the barbs and the projection represent potential sources of injury to a user.

U.S. Pat. No. 4,718,889 issued to Blasius, Jr. et al. discloses the use of a resilient cushion positioned between the end of the stem and the absorbent covering. This resilient cushion is intended to provide some degree of protection against injury in the event that the stem does protrude through the absorbent covering. However, the stem of this prior art device can still protrude through its absorbent covering, leaving only the thin resilient cushion to protect delicate body tissue from injury.

U.S. Pat. No. 3,368,549 discloses a T-shaped projection to secure a culture medium to a stem. While the swab of this prior art patent is not intended to clean body tissue, it does come into intimate contact with such tissue during diagnostic culture use. The T-shaped projection near its distal end is used to secure a culture medium to the stem, which projection could protrude through the culture medium and cause damage to delicate body tissue.

As such, although the prior art has recognized to a limited extent the problem of potential injury caused by the stem of the swab protruding through the absorbent covering during use, the proposed solutions to date have been ineffective in providing a satisfactory remedy. Further, the problem of potential damage to the ear drum caused by entrance of the swab into the ear canal, although long being recognized, has heretofor never been addressed.

As such, there exists a substantial need in the art for an improve swab which eliminates damage to the ear canal as well as reduces the possibility of damaging soft tissue during prolonged use.

SUMMARY OF THE INVENTION

The present invention specifically addresses and alleviates the above mentioned deficiencies associated with the prior art. More particularly, the present invention comprises an improved swab having cotton covered enlarged distal ends and an elongated stem for use in cleaning the outer portion of the ear and/or in applying cosmetics and the like to soft tissue. Positioned at each of the distal ends of the swab beneath the cotton coverings is a flat disc which is sized to prevent entry of the swab into the human ear canal. The flat disc also prevents the stem from protruding through the cotton covering and causing injury during prolonged use.

The swabs can advantageously be manufactured in two sizes, i.e. adult and children. A swab with a larger disc would be sized to prevent entry of the swab into an adult's ear canal while a swab with a smaller disc would be sized to prevent entry of the swab into a child's ear canal.

The flat disc adds support to its associated absorbent covering, thereby preventing compaction of the absorbent covering during usage. This eliminates the possibility of having the absorbent covering becoming so compacted that its size is reduced to a point where it could enter the ear canal.

Further, the present invention is provided an absorbent covering having a greater amount of surface area than prior art swabs. This greater amount of surface area increases the utility of the swab.

A principal object of the present invention is therefore to provide an improved swab which is incapable of entering the human ear canal and thereby causing injury.

A further object of the invention is to provide an improved swab which reduces the possibility of injury to delicate body tissue caused by the stem protruding through the absorbent covering.

A further object of the invention is to provide an improved swab having a tip end which resist deformation and compaction during use, thereby eliminating the possibility that the tip will be reduced in diameter and fit into the ear canal.

A further object of the invention is to provide an improved swab having a greater surface area of absorbent material so as to provide greater utility than the prior art swabs.

Therefore, in response to this present need in the art, an improved swab is provided which not only passively prevents the user from being injured due to misuse, but also is safer and more effective even when used correctly.

BRIEF DESCRIPTION OF THE DRAWINGS

These and other features of the invention will become more apparent to those skilled in the art upon reading and consideration of the following description of a preferred embodiment and the accompanying drawings wherein.

DETAILED DESCRIPTION OF A PREFERRED EMBODIMENT

Figure 1:
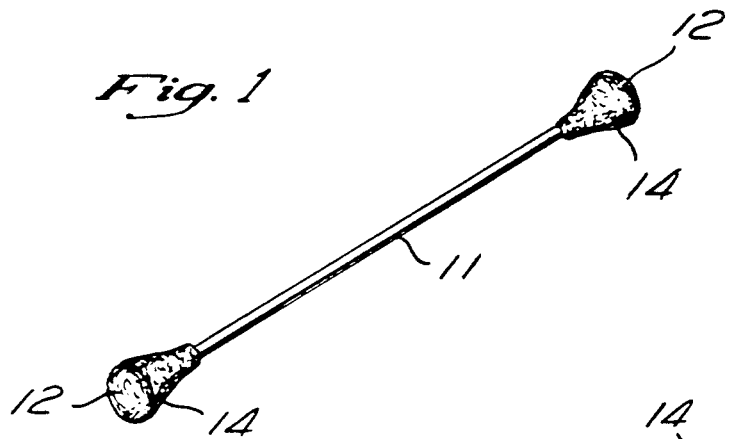
FIG. 1 is a perspective view of the preferred embodiment of the improved swab.
Figure 2:
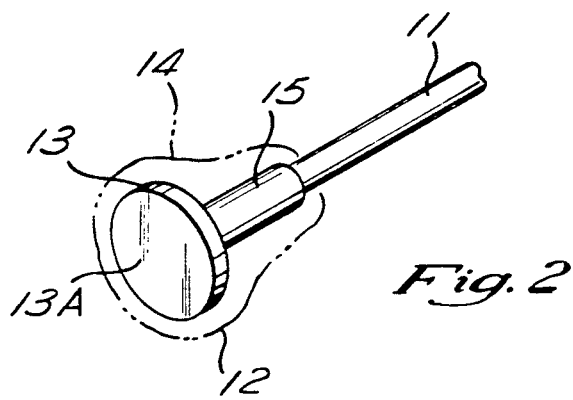
FIG. 2 is a close-up perspective view of one distal end of the preferred embodiment of the improved swab.
Figure 3:
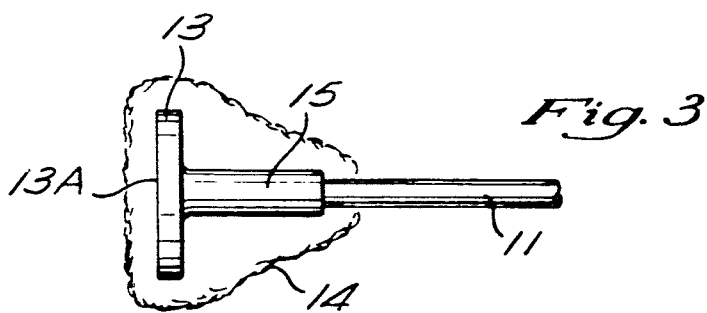
FIG. 3 is a side view of one distal end of the preferred embodiment of the improved swab.

The improved swab of the present invention is illustrated in FIGS. 1 through 3 which depicts a preferred, although not limited to, embodiment of the invention.

Figure 4:
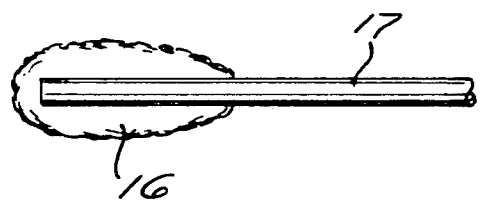
FIG. 4 is a side view of one distal end of a prior art swab.

FIG. 4 depicts a conventional prior art swab. The absorbent material 16 of the prior art swab is typically applied directly to the stem 17. Occasionally an adhesive is used to better secure the absorbent material 16 to the swab 17.

The prior art swab is sized so that it can easily enter the human ear canal, creating the potential for serious injury. Also, there is typically no means provided to prevent the stem 17 of the prior art swab from protruding through the absorbent material 16 during use and thereby causing damage to delicate body tissue.

FIG. 1 depicts the improved swab of the present invention composed of a stem 11 and two enlarged distal ends 12 covered by an absorbent material such as cotton. As can be seen from FIG. 2, the cotton covered distal ends are preferably tapered, growing greater in diameter as the end of the stem is approached. The distal ends are also preferably formed flat on their outermost surfaces. This unique shape facilitates easy use while resisting distortion. The flat outer surface provides ample surface area for cleaning. Since the end is blunt, there is no tendency for it to become compacted under moderate pressure as occasioned with prior art swabs. Prior art swabs tend to become blunt as moderate pressure is applied. This lead to distortion of the absorbent covering, often causing the absorbent covering the detach from the stem or allowing the stem to protrude through the absorbent covering.

FIG. 2 is an enlarged view of one distal end of the improved swab which shows an enlarged disc 13 positioned beneath the cotton covering 14. The disc 13 typically is formed having a substantially flat planar outer surface 13A, although other configurations, such as convex and/or concave curvilinear configurations are contemplated. The disc 13 is additionally provided with an integral sleeve 15 by which attachment is made to the stem 11. Alternatively, the disc 13 and the stem 11 could be formed as a single unit during manufacture as by way of conventional injection molding techniques.

FIG. 3 shows a side view of the distal end of the improved swab depicted in FIG. 2. The cotton covering is applied to the flat disc 13 and its integral sleeve 15 so that both are completely covered. An adhesive may be used to better secure the cotton covering 14 to the flat disc 13 and the sleeve 15.

The flat disc 13 is typically formed of a substantially rigid but soft supple thermoplastic material and is specifically sized so that it prevents the distal end 12 of the improved swab from entering the human ear canal. That is, the outside diameter of perimeter dimensions of the flat disc 13 is sized greater than the typical diameter of the human ear canal. For adult usage, the applicant has found that suitable sizing comprises a diameter of approximately 0.50 to 0.80 inch and typically 0.75 inch while for child usage a diameter of approximately 0.20 to 0.40 inch and typically 0.25 inch is preferred.

The flat disc 13 also provides support to the cotton covering 14 during use. This completely overcomes the problem of having the stem 11 protrude through the cotton covering 14 while cleaning a delicate part of the human body, such as the outer ear.

The greater surface are of the cotton covering 14, as compared to prior art swabs, provides for greater absorption. This gives each swab a greater amount of utility than the prior art swabs.

The improved swab is used by grasping the stem 11 near one distal end 12 and using the absorbent cotton covering on the distal end to clean with. The absorbent cotton covering is wiped gently over the outer surface of the ear. This motion will remove dirt and wax from the outer portion of the ear. Due to the diameter of the disc 13 being greater than the diameter of the ear canal, the improved swab cannot be inserted into the ear canal, so any temptation to do so is removed. The greater surface area of the improved swab permits it to be used more extensively than could be done with a prior art swab. That is, by rotating the swab repeatedly, fresh cotton is continually provided to continue with the cleaning task until the entire absorbent cotton covering is soiled.

It is understood that the exemplary swab described herein and shown in the drawings represents only a presently preferred embodiment of the invention. Indeed, various modifications and additions may be made to such embodiment without departing from the spirit and scope of the invention. For example, only one end of the swab may be provided with the disc 13 while the shape of the thin disc 13 could be modified significantly without affecting its function. Likewise, the attachment of the disc 13 to the stem 11 could be accomplished by various means. Thus, these and other modifications and additions may be obvious to those skilled in the art and may be implemented to adapt the present invention for use in a variety of different applications.

What is claimed is:

1. An improved swab comprising:
   an elongate stem;
   a stop member positioned on at least one end of said stem, said stop member comprising:
   (a) a disc portion having an outer surface and an inner surface; and
   (b) a connector portion for receiving said at least one end of said stem;
   an absorbent covering surrounding said stop member;
   wherein said disc portion is mixed having a peripheral dimension sufficient to prevent entry of said disc portion into a human ear canal and said connector portion is formed in a manner operable to prevent any portion of said stem from protruding through said disc portion and entering said ear canal.

2. An improved swab according to claim 1 wherein said connector portion comprises an elongate sleeve extending axially from said inner surface of said disc portion, said sleeve being sized and configured to receive said at least one end of said stem.

3. An improved swab according to claim 1 wherein the absorbent material is secured to the stop member with an adhesive.

4. An improved swab according to claim 3 wherein the absorbent material is cotton.

5. An improved swab according to claim 3 wherein said disc portion is formed having a substantially flat planar outer surface.

6. An improved swab according to claim 1 wherein said stop member is formed as in integral portion of said stem.

7. An improved swab according to claim 6 wherein the absorbent material is secured to said stop member with an adhesive.

8. An improved swab according to claim 7 wherein the absorbent material is cotton.

9. A method for manufacturing an improved swab comprising the steps of:
   (a) positioning a stop member on at least one end of a stem, wherein said stop member comprises:
      a disc portion having an outer surface and an inner surface, and a connector portion for receiving said at least one end of said stem, said disc portion being sized having a peripheral dimension sufficient to prevent entry of said disc portion into a human ear canal and said connector portion being formed in a manner operable to prevent any portion of said stem from protruding through said disc portion and entering said ear canal;
   (b) covering said stop member with an absorbent material.

10. A method for manufacturing an improved swab according to claim 9 further comprising the step of applying an adhesive to said stop member prior to covering said stop member with absorbent material.

* * * * *